United States Patent [19]

Walon

[11] 4,235,965

[45] Nov. 25, 1980

[54] STARCH HYDROLYSIS AT HIGH DRY SUBSTANCE

[75] Inventor: Raoul G. P. Walon, Brussels, Belgium

[73] Assignee: CPC International Inc., Englewood Cliffs, N.J.

[21] Appl. No.: 951,538

[22] Filed: Oct. 16, 1978

Related U.S. Application Data

[63] Continuation of Ser. No. 793,216, May 2, 1977, abandoned.

[30] Foreign Application Priority Data

May 12, 1976 [BE] Belgium .............................. 2155022

[51] Int. Cl.$^3$ ........................ C12P 19/22; C12P 19/14
[52] U.S. Cl. ....................................... 435/95; 435/99; 426/48; 426/661
[58] Field of Search .................. 195/7, 11, 31 R, 115; 426/48, 658, 651; 127/32; 435/99, 95

[56] References Cited

U.S. PATENT DOCUMENTS

| 3,450,549 | 6/1969 | Schwalbe | 127/32 X |
| 3,922,196 | 11/1975 | Leach et al. | 195/31 R |
| 3,922,198 | 11/1975 | Kuske et al. | 195/31 R |
| 3,922,199 | 11/1975 | Hebeda et al. | 195/31 R |
| 3,922,200 | 11/1975 | Walon | 195/31 R |
| 3,962,465 | 6/1976 | Richter et al. | 426/48 |
| 4,014,743 | 3/1977 | Black | 195/31 R |

Primary Examiner—Thomas G. Wiseman
Attorney, Agent, or Firm—Stanley M. Parmerter; Janet E. Price

[57] ABSTRACT

Aqueous slurries of liquefied and at least partially solubilized starch of high solids concentration (substantially greater than 40%, by weight) are prepared directly by adding gradually, to an aqueous starch hydrolysate having not greater than 40% solids, granular starch in the presence of a bacterial α-amylase, under non-gelatinizing conditions, while gradually raising the temperature to not above 90° C. As a final step, the temperature can be brought to 90° C. or higher to liquefy any remaining starch.

14 Claims, No Drawings

STARCH HYDROLYSIS AT HIGH DRY SUBSTANCE

This is a continuation of copending application Ser. No. 793,216, filed May 2, 1977, abandoned.

BACKGROUND OF THE INVENTION

This invention relates to the preparation of aqueous slurries of fully liquefied, and at least partially solubilized, starch, having extremely high solids concentrations; i.e., substantially greater than 40%, by weight.

Starch is liquefied and/or solubilized for many reasons, such for the preparation of malto-dextrins and as the first step in saccharification processes to form starch syrups, dextrose, levulose, and the like. It is generally desirable to obtain such aqueous slurries having the highest dry substance concentration possible, but the maximum concentration obtainable (using conventional equipment and unmodified starch) is about 40% solids. This is because, of course, the starch undergoes gelatinization under conventional liquefaction processes with an attendant sharp increase in the viscosity (referred to as the viscosity peak), and a gelatinized unmodified starch paste of more than 40%, dry substance, is too viscous to be processed in conventional equipment. It is customary practice, therefore, to liquefy the starch at a solids content of not over 40%, and eventually employ a separate evaporation step to bring the solids concentration to the desired point. Evaporation, of course, requires special equipment and employs a good deal of energy.

It is known that starch can be solubilized with α-amylase under non-gelatinizing conditions and recent developments (see, for example, U.S. Pat. Nos. 3,922,199 to Hebeda et al, 3,922,200 to Walon et al, 3,922,198 to Kuske et al and 3,922,196 to Leach et al) show that starch can be effectively solubilized with bacterial α-amylase at temperatures higher then its "normal" gelatinization temperature without any observable gelatinization taking place.

These recently developed processes are limited to starch slurries of 40% or lower (unless special equipment is employed) and furthermore, when working at temperatures substantially above the normal gelatinization temperature (e.g. at 75° C. for corn starch) it is necessary first to prepare the aqueous slurry of starch and enzyme at a lower temperature and then heat it to the final desired temperature, if gelatinization is to be avoided. If one adds starch and α-amylase directly to hot water, having a temperature above the normal gelatinization temperature of the starch, the starch promptly gelatinizes. Surprisingly, however, in the process of the instant invention, when the fresh granular starch is added to the aqueous liquefied starch slurry at temperatures of as high as 75° C.–85° C. or even above, no observable gelatinization, with attendant viscosity peak, occurs. Because of this surprising phenomenon it is possible to "build-up" the solids content of a fully liquefied starch slurry to the levels aforementioned.

DETAILED DESCRIPTION OF THE PREFERRED EMBODIMENT

I have discovered a process whereby aqueous slurries of liquefied and substantially solubilized starch having exceptionally high solids contents; i.e., up to 70% by weight or higher, can be prepared using conventional equipment and without the necessity of a separate evaporation step. In accordance with my process one starts with an aqueous slurry of a starch hydrolysate (having a D.E. of about 1 to about 25) at a solids concentration of 40% by weight or lower. This starting material can be prepared in any conventional manner as by acid hydrolysis, acid-enzyme hydrolysis, enzyme hydrolysis, etc. Alternatively, one can start with a dry starch hydrolysate and dissolve it in water to a solids content of up to 40%.

To this starting material is then added, gradually, preferably in the form of successive increments, fresh granular starch, in the presence of a bacterial α-amylase, under conditions which do not cause any observable gelatinization of the starch, with the attendant rapid increase in viscosity which is characteristic of the gelatinization of starch. At the beginning of the process of adding the fresh starch the temperature must be held below the normal geletinization temperature, of course, in order to avoid gelatinization. As the fresh starch is added, and liquefied by the action of the α-amylase, the temperature may be gradually raised up to well above the "normal" gelatinization of the starch, without any observable gelatinization and "viscosity peak". By this method of gradually adding and liquefying the starch, under non-gelatinizing conditions, the solids content of the slurry can be "built-up" to concentrations of up to 70%, by weight, or even higher, in conventional equipment without any viscosity problems. Desirably, after the last of the fresh starch has been added and substantially liquefied and solubilized by the alpha-amylase, the temperature is raised to at least 90° C. (preferably between 90° C. and 105° C., although temperatures up to 150° C. are suitable) in order to liquefy and substantially solubilize any remaining starch.

During the process of adding and liquefying fresh starch, the alpha-amylase may be added as needed. However, the most practical method is to provide sufficient alpha-amylase in the starting slurry to liquefy all of the starch to be added, thereby avoiding additional steps of adding additional enzymes throughout the process. The conditions of the process are such that this can readily be done, without deleterious effect upon the alpha-amylase.

The temperature at the start of the starch addition process should be one suitable for the optimum alpha-amylase action, without, of course, gelatinizing the starch; a temperature of 60° C. is suitable for most starches. As the starch is gradually added and liquefied, the temperature may be advantageously raised up to about 85° C., and finally to 90° C. or above, without any observable gelatinization taking place.

The choice of bacterial alpha-amylase is not critical, except the enzyme should be one which retains its activity at the temperatures employed. Preferred sources of suitable alpha-amylases including certain species of the Bacillus microrganism, such as, *Bacillus subtilis, Bacillus licheniformis, Bacillus coagulans* and *Bacillus amyloliquefaciens.* Suitable α-amylases are described in Austrian Patent Appln. No. 4836/70 and in U.S. Pat. No. 3,697,368. Especially suitable α-amylases are those derived from *Bacillus licheniformis,* as described in the Austrian application. Particularly preferred is that α-amylase derived from *Bacillus licheniformis* strain NCIB 8061; other specific microorganisms include *Bacillus licheniformis* strains NCIB 8059, ATCC 6598, ATCC 6634, ATCC 8480, ATCC 9945A, and ATCC 11945. These aforementioned enzymes are unusually effective in the liquefaction of granular starch; i.e., in the liquefaction of starch in its granular form, without prior or concurrent gela tinization. One such enzyme, which is particularly suitable in the practive of the invention, is identified by the trade name "Thermamyl", available from Novo Enzyme Corporation, Mamaroneck, New York. Thermamyl is characterized by the following properties:

(a) it is thermally stable;
(b) it is active throughout a wide range of pH; and,
(c) its activity and heat stability are less dependent than other α-amylase on the presence of added calcium ion.

Typical analysis of three different Thermamyl preparations are as follows:

|  | Thermamyl 60 | Thermamyl 120 | Thermamyl |
|---|---|---|---|
| Dry substance, % | 35.4 | 98.8 | 94.6 |
| α-amylase activity, U/g (as is) | 1,156 | 2,105 | 9,124 |
| Protein, % d.b. | 26.5 | 21.2 | 21.2 |
| Ash, % d.b. | 60.1 | 91.2 | 64.4 |
| Calcium, % d.b. | 0.04 | 0.72 | 4.9 |
| Sodium, % d.b. | 12.3 | 12.2 | — |

Still other suitable alpha-amylases which are available include the following:

TABLE I

| Enzyme Preparation | Company | Form | Activity |
|---|---|---|---|
| Rhozyme H-39 | Rohm & Haas | Powder | 4,874 U/g |
| Takamine HT-1000 | Miles | Powder | 3,769 U/g |
| Tenase | Miles | Liquid | 2,043 U/ml |
| Dex-Lo MM | Wallerstein | Liquid | 1,213 U/ml |
| Novo SP-96 | Novo | Powder | 7,310 U/g |
| Novo B. Subtilis | Novo | Liquid | 1,599 U/ml |
| Kleistase GM-16 | Daiwa Kasai | Powder | 26,593 U/g |
| Kleistase L-1 | Daiwa Kasai | Liquid | 1,918 U/ml |
| Rapidase SP-250 | Societe "Rapidase" France | Powder | 11,655 U/g |
| Maxamyl LX 6000 | Gist-Brocades | Liquid | 13,300 U/ml |

The alpha-amylase activity of an enzyme is determined as follows:

The enzyme is allowed to react with a standard starch solution under controlled conditions. Enzyme activity is determined by the extent of starch hydrolysis, as reflected by a decrease in iodine-straining capacity, which is measured spectrophotometically. The unit of bacterial alpha-amylase activity is the amount of enzyme required to hydrolyze 10 mg. of starch per minute under the conditions of the procedure. The method is applicable to bacterial alpha-amylases, including industrial preparations, except materials which possess significant saccharifying activity.

From 0.3 to 0.5 of solid sample or from 0.3 to 1.0 ml. of a liquid sample is dissolved in a sufficient quantity of 0.0025 M. aqueous calcium chloride to give an enzyme solution containing approximately 0.25 unit of activity per ml.

A mixture of 10 ml. of 1% Lintner starch solution, equilibrated to 60° and 1 ml of the enzyme sample to be tested is mixed and held in a constant temperature bath for exactly 10 minutes. A 1-ml. sample is removed and added to a mixture of 1 ml of 1 M aqueous hydrochloric acid and about 50 ml of distilled water. The iodine-staining capacity of such acidified sample then is determined by adding 3.0 ml of 0.05% aqueous iodine solution, diluting to 100 ml with distilled water, and mixing well.

The absorbance of the solution, relative of that of distilled water, is measured at 620 mm. in a 2-cm cell. (A similar measurement is made of the standard starch solution) to provide a blank absorbance. The enzyme activity, in units: gram or/ml. is equal to:

$$\frac{(\text{Blank Absorbance} - \text{Sample Absorbance}) \times \text{Dilution Factor} \times 50}{\text{Blank Absorbance} \times 10 \times 10}$$

The amount of alpha-amylase employed is, of course, the amount necessary to liquefy all of the granular starch, which can generally be within the range of from about 0.5 to about 25 activity units per gram of starch (dry basis), the minimum amount depending upon the particular starch being liquefied. Amounts greater than 25 U/g of starch can be used, but with no practical advantage. As mentioned previously, it is preferred to add the entire "dose" of alpha-amylase at the beginning of the process, although it can be added in small amounts throughout the process, as needed, if desired. The pH during the liquefaction of the starch must, of course, be such as to obtain the optimum activity of the alpha-amylase; this is generally within the range of from 5 to 7.5, preferably about 6.

The specific conditions of rate of addition of the starch, amount added at any given time, and temperature adjustments are such as to avoid observable gelatinization and to prevent the viscosity from becoming too high to be conveniently handled. The complementary additions of starch can be made at any point where a sufficient ratio of the previously added starch has been solubilized to a degree where the subseqent addition does not bring a too high viscosity. When using conventional equipment, therefore, the process should be practiced in such a way as to avoid viscosities much above about 3,000 cps.

The invention can be advantageously practiced at viscosities higher than about 3,000 cps. if equipment is used which is capable of handling these higher viscosities. However, one of the principal advantages of the invention lies in the conservation of energy, by avoiding the necessity of using such special equipment, eliminating or minimizing evaporation steps, etc. Therefore, it is preferred that the invention be practiced in conventional equipment.

In the practice of the invention substantial liquefaction and solubilization of a high solids slurry is accomplished by the time the temperature has reached about 80° C.-85° C., and such a product can be recovered directly for use. However, it is desirable to add the additional final step of raising the temperature to at least 90° C., which effectively liquefies and substantially solubilizes any remaining starch.

The recovered high-solids slurry can be used "as is"; i.e., in any of the customary applications of malto-dextrins or other liquefied starches, or can be used as a substrate for further saccharification.

If further saccharification is desired one merely makes the necessary temperature and pH adjustments, adds the appropriate saccharifying enzyme or enzymes, and permits the saccharification to proceed in conventional manner. For example, if dextrose or a dextrose-containing hydrolyzate is desired glucoamylase is added; to prepare a levulose-containing syrup glucose-isomerase can be added subsequent to or simultaneously with the action of the glucoamylase, for a high-maltose product beta-amylase, with or without alpha, 1-6 glucosidase is employed; etc. Furthermore, one or more saccharifying enzymes (e.g., glucoamylase or beta-amylase) may be added at the start of, or during, the liquefaction process in addition to the bacterial alpha-amylase, to good advantage, because the presence of such an enzyme will increase the solubilization of the starch.

The invention can be practiced with any variety of starch; e.g., corn starch, wheat starch, potato starch, rice starch, the various waxy starches consisting primarily of amylopectin, the high amylose starches, etc., as well as starches which have undergone physical and/or chemical modification or derivatization. Starch-containing materials such as flours, meals, etc., can also be used.

The following examples will illustrate the practice of the invention; it is understood that the examples are not intended to limit the scope of the invention. Unless otherwise stated, all percentages in the examples and in the claims are by weight. The dry substance values were obtained with a Zeiss Refractometer.

EXAMPLE 1

This example illustrates the practice of the invention including the subsequent step of saccharifying the resulting high solids starch slurry to a high maltose hydrolysate.

400 grams of potato starch, having 18% moisture, was added to 600 cc of tap water to give a starch suspension of about 33% dry substance. To this was added 0.22 gram of $CaCl_2$, 0.022 gram NaCl and 2.5 g. Thermamyl 60 $\alpha$-amylase. The pH was 6.2. The temperature was brought to 60° C. and the product was held at this temperature, with agitation for 60 minutes. At the end of this time, the product had the following characteristics:

Total dry substance—33%
Solubles, total—25%
Solubles, dry basis—75.8%
D. E. of solubles—9.1%
Viscosity—60 cps at 60° C.

The temperature was raised to 75° C. over a period of 45 minutes; at the end of this time the viscosity had dropped to 30 cps. 500 grams of starch was then added to the slurry; no observable gelatinization took place. The product was then held for 60 minutes at 75° C., after which time it had the following characteristics:

Total dry substance—52%
Solubles, total—49%
Solubles, dry basis—94.2%
D. E. of solubles—16
Viscosity—400 cps at 75° C.

The temperature was raised to 80° C. over a period of 20 minutes, after which 500 grams of starch was added; again, no observable gelatinization took place. The product was held at 80° C., with continued agitation, for 90 minutes, after which it had the following characteristics:

Total dry substance—58%
Solubles, total—52%
Solubles, dry basis—89.6%
D. E. of solubles—17
Viscosity—720 cps at 80° C.

The temperature was then raised to 95° C. over a period of 30 minutes, and then cooled to 75° C. The final product had the following characteristics:

Total dry substance—66.4%
Solubles, total—65.9%
Solubles, dry basis—99.2%
D. E. of solubles—18.2%
Viscosity—680 cps at 75° C.

The temperature was then brought to 60° C. and the pH adjusted to 5.2, and 0.3 grams of $\beta$-amylase (Biozyme M, of Amano Pharmaceuticals, Japan) was added. The product was incubated for 12 hours, resulting in a maltose-containing hydrolysate having the following composition:

Dry substance—67.2%
D. E.—43.4
Dextrose—3.1%
Maltose—56.4%
DP3—12.8%
Higher saccharides—27.7%

EXAMPLE 2

In this example a commercially available malto-dextrin, having a D.E. of 19.5 and a solubles content of 98.5, was used as the starting material. 460 grams of the malto-dextrin was dissolved in 600 cc of water, giving a slurry of slightly above 40% dry substance. The pH was adjusted to 6.2, the temperature was raised to 60° C., and 0.7 grams of Thermamyl 60 $\alpha$-amylase and 0.06 gram $CaCl_2$ 1 were added. 400 grams of potato starch were then added, and the suspension was held at 60° C. with agitation for 3 hours; it was then raised to 75° C. over a period of 30 minutes, and held at that temperature for 2 additional hours. At the end of that time, the product had the following characteristics:

Total dry substance—53%
Solubles, dry basis—94.2%
D. E. of solubles—18.2%
Viscosity—780 cps at 75° C.

400 grams of starch were then added at 75° C. and the product held for three hours; the temperature was then raised to 80° C. over a period of 30 minutes, the product was held for one hour at that temperature, the temperature was then raised to 95° C. over a period of 30 minutes and then cooled to 75° C. The product had the following characteristics:

Total dry substance—56.1%
Solubles, dry basis—97.2%
D. E. of solubles—17.4%
Viscosity—1,140 cps at 75° C.

EXAMPLE 3

A 34% aqueous suspension was prepared by adding 400 grams of waxy corn starch, containing 14% moisture, to 600 ml water. To this 0.15 gram $CaCl_2$, 0.015 gram NaCl and 0.8 gram Thermamyl 60 $\alpha$-Amylase were added. The pH was 6.2. The temperature was raised to 60° C. and the product held at that temperature, with stirring, for one hour. At the end of that time the product had the following characteristics:

Total dry substance—34.4%
Solubles, dry basis—27.6%
D. E.—5.5%
Viscosity—37 cps

The temperature was raised to 75° C. over a period of 30 minutes, and an additional 400 grams of starch was added. The product was held at that temperature for 90 minutes, after which it had the following characteristics:

Total dry substance—51%
Solubles, dry basis—55%
D. E.—9.0
Viscosity—1,540 cps

The temperature was brought to 85° C. over a period of 30 minutes, and 200 grams more starch were added and the product held for 90 minutes. It had the following characteristics:
  Total dry substance—53.8%
  Solubles, dry basis—79%
  D. E.—12.2
  Viscosity—1,350 cps The temperature was then brought to 95° C. over a period of 30 minutes, after which the final product had the following characteristics:
  Total dry substance—58%
  Solubles, dry basis—95%
  D. E.—13.6
  Viscosity—900 cps at 95° C.

EXAMPLE 4

400 grams of corn starch at 12% moisture was added to 600 ml of water, to give a 35% suspension. To this 1.6 gram Thermamyl 60 α-amylase, 0.15 gram CaCl$_2$ and 0.015 gram NaCl were added. The pH was 6.2. The temperature was brought to 60° C. and held for 2½ hours. At the end of that time the product had the following characteristics:
  Total dry substance—35.2%
  Solubles, dry basis—56%
  D. E.—7.3
  Viscosity—22 cps While maintaining the temperature at 60° C., 100 grams more corn starch were added in two increments of 50 grams each, at 10 minute intervals. 10 minutes after the second addition of starch the product had the following characteristics:
  Total dry substance—39%
  Solubles, dry basis—51%
  D. E.—7.7
  Viscosity—28 cps The temperature was raised to 70° C. and again 100 grams starch was added in two increments of 50 grams each at 10 minutes intervals. The temperature was raised to 75° C., after which 100 additional grams were added in two increments of 50 grams each, at 15 minute intervals.

Then an additional 100 grams of starch, in two increments of 50 grams each were added at 75° C. at intervals of 25 minutes. 25 minutes after the second addition, the product had the following characteristics:
  Total dry substance—51%
  Solubles, dry basis—87%
  D. E.—12.6
  Viscosity—620 cps The temperature was then raised to 90° C. over a period of 30 minutes; the final product had the following characteristics:
  Total dry substance—51%
  Solubles, dry basis—94%
  D. E.—13.4
  Viscosity—920 cps

EXAMPLE 5

A 34% aqueous suspension was prepared by adding 400 grams of tapioca starch, containing 13.8% moisture to 600 ml water. To this 0.15 gr CaCl$_2$; 0.015 gr NaCl and 0.8 gr Thermamyl 60 α-amylase were added.

The pH was 6.2. The temperature was raised at 60° C. and the product held at that temperature with stirring for one hour. At the end of that time the product had the following characteristics:
  Total dry substance—34.8%
  Solubles, dry basis—26.7%
  D. E.—3.8
  Viscosity—28 cps The temperature was raised to 75° C. over a period of 30 minutes, and an additional 400 gr of starch were added. The product was held at that temperature for 90 minutes, after which it had the following characteristics:
  Total dry substance—49.3%
  Solubles, dry basis—53.2%
  D. E.—14.6
  Viscosity—124 cps The temperature was brought to 85° C. over a period of 30 minutes, and 200 gr more starch were added and the product held for 80 minutes. It had the following characteristics:
  Total dry substance—53.8%
  Solubles, dry basis—89.4%
  D. E.—15.2%
  Viscosity—320 cps 200 grams more starch were added and the product held for 90 minutes. It had the following characteristics:
  Total dry substance—58.2%
  Solubles, dry basis—91%
  D. E.—15.7%
  Viscosity—620 cps 200 grams more starch were added and the product held for 90 minutes. It had the following characteristics:
  Total dry substance—60.2%
  Solubles, dry basis—91.8%
  D.E.—16.3
  Viscosity—872 cps The temperature was then brought to 95° C. over a period of 30 minutes, after which the final product had the following characteristics:
  Total dry substance—62.3%
  Solubles, dry basis—94.2%
  D.E.—17.5
  Viscosity—652 cps

EXAMPLE 6

Of all of the starches tested (i.e. potato, waxy corn, regular corn, tapioca and wheat starches) it was found that wheat starch (probably because of its low gelatinization temperature and the structure of the wheat starch granule) was the most difficult to process in accordance with the invention. When conditions similar to those set forth in the previous examples were applied to wheat starch, gelatinization, with viscosity "peaks" of 20,000 cps. and higher, occurred at temperatures of about 75° C. Although such viscosities can be handled if special equipment is used, the maximum advantages of the process of the invention are realized by avoiding the use of such special equipment. It was found that high-solids slurries of liquefied wheat starch can be prepared in accordance with the process of the invention, with no observable gelatinization and no attendant viscosity peak, by increasing substantially the amount of alpha-amylase employed. It was found that a particularly advantageous method consists of using a combination of alpha-amylases, i.e. Thermamyl 60 (derived from *Bacillus licheniformis*) and Maxamyl (derived from *Bacillus subtilis.*) Following is a description of a suitable method for processing wheat starch in accordance with the invention.

The initial aqueous slurry was prepared by adding 400 gms of wheat A starch, containing 11.0% moisture, to 600 ml of demineralized water, adding 0.15 g. CaCl₂, 0.015 g. NaCl, 6.4 g. Thermamyl 60 and 0.70 g. Maxamyl alpha-amylase, raising the temperature to 50° C. and holding the product at that temperature with stirring for one hour. The pH was 6.2. The product had the following characteristics:

Total dry substance—35.6%
Solubles, dry basis—10.5%

No observable gelatinization, or viscosity increase, took place. During this experiment the viscosities were not actually measured, but visual observations were made. Throughout the following process no viscosity increases were observed.

The temperature was raised to 60° C. over a period of 30 minutes; during this time when the temperature reached 55° C., an additional 50 gms of starch was added, and a further 50 gms was added when the temperature reached 58° C. The product was held at 60° C. for 40 minutes, after which it had the following characteristics:

Total dry substance—40.5%
Solubles, dry basis—19.8%

Another increment of 50 gms of starch was added and the temperature raised to 62° C. and held at that temperature for 15 minutes. Another 50 gms starch was then added, the temperature was then raised to 65° C. over a period of 30 minutes, after which 50 gms more starch was added. The temperature was held at 65° C. for 15 minutes, after which the product had the following characteristics:

Total dry substance—46.3%
Solubles, dry basis—32.1%

The temperature was then raised to 69° C. over a period of 1 hour, after which an additional 50 gms of starch was added. The temperature was then raised to 72° C. over a period of 15 minutes, and held at that temperature for 15 minutes more, after which the product had the following characteristics:

Total dry substance—47.9%
Solubles, dry basis—38.9%

The temperature was then raised to 85° C. over a period of 1 hour and the product held at that temperature for 30 minutes. The pH was adjusted to 7.2 and the product was boiled (±100° C.) for 10 minutes. The final product had a total dry substance of 48.8% and gave a negative starch test.

While the invention has been described in connection with specific embodiments thereof, it will be understood that it is capable of further modification, and this application is intented to cover any variations, use or adaptions of the invention following, in general, the principles of the invention and including such departures from the present invention disclosure as come with the known or customary practice in the art to which the invention pertains and as may be applied to the essential features hereinbefore set forth, and as fall within the scope of the invention.

I claim:

1. A process for preparing an aqueous slurry of a liquefied and substantially solubilized starch comprising the steps of:
   (a) preparing an aqueous slurry of starch hydrolyzate having a D.E. of about 1 to about 25 and a solids concentration of less than 40% by weight;
   (b) gradually adding granular starch to said slurry of starch hydrolyzate, held at a temperature below the normal gelatinization temperature of the starch, in the presence of sufficient bacterial alpha-amylase to liquefy the granular starch;
   (c) gradually raising the temperature of the mixture from 60° C. to 90° C. during the addition of further increments of starch, maintaining an effective temperature to insure non-gelatinizing conditions for the added starch;
   (d) termininating the addition of starch when the total dry substance of the slurry is between 47% and 70% by weight; and
   (e) recovering the slurry when the starch is substantially solubilized and has a dextrose equivalent (D.E.) of from about 9.1 to about 17.5.

2. The process of claim 1, wherein the conditions under which the granular starch is added to the slurry are such as to avoid, at all times during the process, an increase in the viscosity of the starch to above 3,000 cps.

3. The process of claim 1, and further including the step of raising the temperature of the final slurry to between 90° C. and 150° C. in order to liquefy any remaining starch.

4. The process of claim 1, wherein the granular starch is gradually added to the slurry in the form of successive increments, and wherein each increment is substantially liquefied and solubilized by the α-amylase before the next increment is added.

5. The process of claim 1, wherein the initial aqueous slurry is prepared by subjecting an aqueous suspension of granular starch, having a solids content of not more than about 40%, to the action of a bacterial α-amylase, under conditions which liquefy and at least partially solubilize the starch while avoiding gelatinization of the starch.

6. The process of claim 1, wherein the initial aqueous slurry is prepared by dissolving a malto-dextrin into water, at a solids concentration or not greater than about 40%.

7. The process of claim 1, wherein the bacterial α-amylase is derived from a Bacillus microorganism.

8. The process of claim 7, wherein the bacterial α-amylase is derived from a *Bacillus licheniformis* microorganism.

9. The process of claim 1, wherein the pH, during the liquefaction of the starch, is maintained within the range of about 5 to about 7.5.

10. The process of claim 9, wherein the pH is maintained at about 6.

11. The process of claim 1, wherein Step (c) is accompanied by incremental increases in the temperature from a starting temperature of about 60° C. to a final temperature of about 85° C.

12. The process of claim 1, wherein the starch employed is selected from the group consisting of corn starch, potato starch, wheat starch, tapioca starch, and waxy starch.

13. The process of claim 1, including the additional step of subjecting the resulting high solids slurry of liquefied starch to an enzymatic saccharification process.

14. The process of claim 13, wherein the additional saccharification step is performed by bringing the high solids slurry to a temperature of about 60° C. and a pH of about 5.0, adding β-amylase and incubating for a time sufficient to produce a starch hydrolysate having a high maltose content.

* * * * *